US011904034B2

(12) United States Patent
Wang et al.

(10) Patent No.: US 11,904,034 B2
(45) Date of Patent: Feb. 20, 2024

(54) TRANSPARENT SOAP BAR

(71) Applicant: The Procter & Gamble Company, Cincinnati, OH (US)

(72) Inventors: Huan Wang, Singapore (SG); Mingxia Chan, Singapore (SG); Matthew Clair Ehrman, Singapore (SG); Anurag Makrandi, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 129 days.

(21) Appl. No.: 17/832,784

(22) Filed: Jun. 6, 2022

(65) Prior Publication Data

US 2022/0401315 A1 Dec. 22, 2022

Related U.S. Application Data

(60) Provisional application No. 63/209,131, filed on Jun. 10, 2021.

(51) Int. Cl.
A61K 8/00 (2006.01)
A61K 8/02 (2006.01)
A61K 8/23 (2006.01)
A61K 8/34 (2006.01)
A61K 8/36 (2006.01)
A61K 8/41 (2006.01)
A61K 8/44 (2006.01)
A61K 8/46 (2006.01)
A61K 8/49 (2006.01)
A61K 8/60 (2006.01)
A61Q 19/10 (2006.01)

(52) U.S. Cl.
CPC .............. A61K 8/0216 (2013.01); A61K 8/23 (2013.01); A61K 8/345 (2013.01); A61K 8/361 (2013.01); A61K 8/41 (2013.01); A61K 8/44 (2013.01); A61K 8/442 (2013.01); A61K 8/463 (2013.01); A61K 8/4913 (2013.01); A61K 8/60 (2013.01); A61Q 19/10 (2013.01); A61K 2800/262 (2013.01); A61K 2800/522 (2013.01); A61K 2800/596 (2013.01)

(58) Field of Classification Search
CPC ................................ A61K 8/0216; A61K 8/23
See application file for complete search history.

(56) References Cited

U.S. PATENT DOCUMENTS

| 4,468,338 | A | * | 8/1984 | Lindberg | ............. | C11D 3/2086 |
| | | | | | | 510/147 |
| 5,264,145 | A | | 11/1993 | French et al. | | |
| 5,310,495 | A | | 5/1994 | Hill et al. | | |
| 5,962,382 | A | | 10/1999 | Lambino | | |
| 6,297,205 | B1 | | 10/2001 | Saxena et al. | | |
| 7,028,835 | B1 | | 4/2006 | Rajter, Jr. | | |
| 7,544,366 | B1 | * | 6/2009 | Lutz | ...................... | A61Q 19/10 |
| | | | | | | 424/401 |
| 2010/0286011 | A1 | * | 11/2010 | Glenn, Jr. | ............ | A61K 8/0216 |
| | | | | | | 510/455 |
| 2011/0244887 | A1 | | 10/2011 | Dupray et al. | | |
| 2015/0034502 | A1 | | 2/2015 | Dickinson | | |
| 2022/0378255 | A1 | | 12/2022 | Hong et al. | | |

FOREIGN PATENT DOCUMENTS

| CH | 657826 A5 | 9/1986 |
| CN | 201737228 U | 2/2011 |
| CN | 202385925 U | 8/2012 |
| CN | 204323847 U | 5/2015 |
| CN | 205602286 U | 9/2016 |
| CN | 206954712 U | 2/2018 |
| CN | 108438424 A | 8/2018 |
| CN | 209492803 U | 10/2019 |
| DE | 4414131 A1 | 10/1995 |
| EP | 3712082 A1 | 9/2020 |
| GB | 2456548 A | 7/2009 |
| JP | 61038019 U | 3/1986 |
| JP | S6335961 A | 2/1988 |
| JP | 2007253973 A | 10/2007 |
| JP | 4154875 B2 | 7/2008 |
| JP | 2013107645 A | 6/2013 |
| WO | 2007013901 A2 | 2/2007 |
| WO | 2012136502 A1 | 10/2012 |

OTHER PUBLICATIONS

PCT Search Report and Written Opinion for PCT/US2022/032754 dated Sep. 30, 2022 13 pages.

* cited by examiner

Primary Examiner — Necholus Ogden, Jr.
(74) Attorney, Agent, or Firm — Alexandra S. Anoff

(57) ABSTRACT

Described herein, a transparent soap bar for cleaning the skin including a soap surfactant, a synthetic surfactant, a fragrance component, an amine component, an antioxidant salt, wherein the transparent soap bar has a percent transmittance (% T) value of greater than 40% as measured using the method of Measurement of % Transmittance.

15 Claims, No Drawings

# TRANSPARENT SOAP BAR

FIELD OF THE INVENTION

The present application generally relates to a transparent soap bar for cleaning the skin comprising a mixture of a fragrance component and an amine component, its methods and uses.

BACKGROUND OF THE INVENTION

Soap bars remain a popular product form for cleansing skin. Those skilled in the art use the term soap to designate the reaction product of a carboxylic acid with a base, typically a metal hydroxide or carbonate. The resulting salt has both a polar hydrophilic end and a non-polar lipophilic end which facilitates the removal of oils and other non-polar materials from the skin or other surface in the presence of water.

Transparent soap bars are sold in a variety of shapes and degrees of optical clarity. The transparent soap bars have much consumer appeal, as clarity in a soap bar connotes health, purity, mildness and freshness. Typically, transparent soap bars contain tallow and coconut soap, and they can also include varying levels of soaps made from castor oil, safflower oil, or synthetic detergents. Transparent soap bars also contain mixtures of sodium, potassium, and/or triethanolamine soaps. Finally, transparent soap bars generally contain polyols, such as glycerin, propylene glycol, sorbitol or sucrose.

Such transparent soap bars are manufactured by preparing and casting a melt, followed by cooling and solidification, and sometimes by additional aging. Transparent soap bars with alleged optical clarity can be made by combining 35-50 wt. % soap with minimal unsaturation, 30-40 wt. % specific blends of polyols, and 15-25 wt. % water. The soap used in these transparent soap bars have generally a minimum level of unsaturation so as not to promote formation of the liquid crystalline phase on cooling.

However, discoloration has been observed when a perfume has been added to a transparent soap bar comprising some specific ingredients, e.g., piroctone olamine used as an antibacterial active or preservative, or an amphoteric surfactant such as a betaine material used as foam booster, or other types of amine Yellowing of the soap composition has been obtained after adding a fragrance component to an amine component of the soap bar.

There is a need for a specific transparent soap bar to prevent any discoloration and provide acceptable stable clarity.

SUMMARY OF THE INVENTION

A transparent soap bar for cleaning the skin is provided and comprises: from 10 wt. % to 30 wt. % of a soap surfactant by weight of the soap bar, wherein the soap surfactant is selected from the group consisting of alkali or alkaline earth metal, and ammonium salts of $C_6$-$C_{18}$ carboxylic acids; from 1.5 wt. % to 30 wt. % of a synthetic surfactant by weight of the soap bar, wherein the synthetic surfactant is selected from the group consisting of an anionic surfactant, a nonionic surfactant, and mixtures thereof; from 0.01 wt. % to 2 wt. % of a fragrance component by weight of the soap bar, wherein the fragrance component comprises ketone and/or aldehyde fragrance components; from 0.01 wt. % to 5 wt. % of an amine component by weight of the soap bar, wherein the amine component is selected from the group consisting of a primary amine, a secondary amine, a tertiary amine, a substituted or unsubstituted 2-pyridinol N-oxide material, an amphoteric surfactant, and mixtures thereof; preferably wherein the amphoteric surfactant is selected from the group consisting of an amphoacetate, an amphodiacetate, a betaine, and mixtures thereof; from 0.01 wt. % to 0.5 wt. % of an antioxidant salt by weight of the soap bar, wherein the anti-oxidant salt is selected from the group consisting of an alkali metal metabisulfite, an alkali metal sulfite, an alkali metal bisulfite and mixtures thereof; and wherein the transparent soap bar has a percent transmittance (% T) value of greater than 40% as measured using the method of Measurement of % Transmittance as disclosed herein.

Use of an antioxidant salt, wherein the anti-oxidant salt is selected from the group consisting of an alkali metal metabisulfite, an alkali metal sulfite, an alkali metal bisulfite and mixtures thereof for preventing or reducing any discoloration of a transparent soap bar comprising a mixture of a fragrance component and an amine component.

A method for preventing or reducing any discoloration of a transparent soap bar as defined hereinafter, is provided and comprises the steps of, preferably in that order, adding from 0.01 wt. % to 0.5 wt. % of an antioxidant salt by weight of the soap bar, wherein the anti-oxidant salt is selected from the group consisting of an alkali metal metabisulfite, an alkali metal sulfite, an alkali metal bisulfite and mixtures thereof; to a premix comprising: from 10 wt. % to 30 wt. % of a soap surfactant by weight of the soap bar, wherein the soap surfactant is selected from the group consisting of alkali or alkaline earth metal, and ammonium salts of $C_6$-$C_{18}$ carboxylic acids; from 1.5 wt. % to 30 wt. % of a synthetic surfactant by weight of the soap bar, wherein the synthetic surfactant is selected from the group consisting of an anionic surfactant, a nonionic surfactant, and mixtures thereof; from 0.01 wt. % to 2 wt. % of a fragrance component by weight of the soap bar, wherein the fragrance component comprises ketone and/or aldehyde fragrance components; from 0.01 wt. % to 5 wt. % of an amine component by weight of the soap bar, wherein the amine component is selected from the group consisting of a primary amine, a secondary amine, a tertiary amine, a substituted or unsubstituted 2-pyridinol N-oxide material, an amphoteric surfactant, and mixtures thereof; preferably wherein the amphoteric surfactant is selected from the group consisting of an amphoacetate, an amphodiacetate, a betaine, and mixtures thereof; wherein the resulting transparent soap bar has a percent transmittance (% T) value of greater than 40% as measured using the method of Measurement of % Transmittance as disclosed herein.

DETAILED DESCRIPTION OF THE INVENTION

Definitions

In this document, including in all embodiments of all aspects of the present invention, the following definitions apply unless specifically stated otherwise.

All percentages are by weight (w/w) of the respective soap bar, unless otherwise specified. All ratios or percentages are weight ratios or weight percentages unless specifically stated otherwise. "% wt." means percentage by weight. References to "parts" e.g. a mixture of 1 part X and 3 parts Y, is a ratio by weight.

"QSP" or "q.s." means sufficient quantity for 100% or for 100 g. "+/−" indicates the standard deviation. All ranges are inclusive and combinable. The number of significant digits conveys neither a limitation on the indicated amount nor on the accuracy of the measurement.

All measurements are understood to be made under ambient conditions, where "ambient conditions" means at 20° C. at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level ("solids") and do not include carriers or by-products that may be included in commercially available materials.

Herein, "comprising" means that other steps and other ingredients can be included in addition. "Comprising" encompasses the terms "consisting of" and "consisting essentially of". The compositions, methods, and uses of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

As used herein, the articles including "a" and "an" when used in a claim, are understood to mean "one or more" of what is claimed or described.

The terms "include," "includes," and "including," as used herein are meant to be non-limiting.

Where amount ranges are given, these are to be understood as being the total amount of said ingredient in the soap bar, or where more than one species fall within the scope of the ingredient definition, the total amount of all ingredients fitting that definition, in the soap bar.

For example, if the transparent soap bar comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the soap bar.

The term "free of" as used herein means that the transparent soap bar comprises 0% of an ingredient by total weight of the soap bar, thus no detectable amount of the stated ingredient.

The term "substantially free of" as used herein means less than 1%, less than 0.8%, less than 0.5%, less than 0.3%, or less than an immaterial amount of a stated ingredient by total weight of the soap bar.

The term "mixtures" as used herein is meant to include a simple combination of materials and any compounds that may result from their combination.

The term "soap" is used herein in its popular sense, i.e., the alkali metal or alkanol ammonium salts of alkane- or alkene monocarboxylic acids.

The objects of the present invention are to provide transparent soap bars and uses of the products, the structures and the respective compositions as described in the Summary or as described hereinbelow for fulfilling the technical effects or goals as set out herein. These objects and other advantages as may be apparent to those skilled in the art can be achieved through the present invention, which is described in the above Summary of the Invention and Detailed Description of the invention and which is defined in the claims which follow.

Benefits

A transparent soap bar is provided and comprises a mixture of soap surfactant and synthetic surfactant. Synthetic surfactants are typically added to provide favorable lather and forming properties along the unique transparent aesthetics of the transparent soap bar.

However, during a stability test, the presence of an amine component, e.g. piroctone olamine, triethylamine or cocamidopropyl betaine in the soap bar caused significant yellowing or coloration of the soap bar when adding a fragrance component.

The one of more fragrance components comprise aldehyde and/or ketone fragrance components that can react with the amine component to form unwanted byproducts. Such unwanted byproducts may cause chromophore formation and discoloration. As aldehyde and/or ketone fragrance components are commonly used in perfume, the addition of any amine component to the aldehyde and/or ketone fragrance components will result in unacceptable discoloration. Such color shift has even turned relatively stronger as the color absorbance accumulated through the entire thickness of the soap bar.

Without being bound by theory, the inventors of the present invention have surprisingly found that the use of specific antioxidant agents can prevent the unwanted reaction between the amine component and the aldehyde and/or ketone fragrance components. The discoloration prevention or reduction could be assessed by measuring the spectrophotometric parameters for overall color change $\Delta E$.

Transparent Soap Bar

A transparent soap bar for cleaning the skin is provided and comprises: from 10 wt. % to 30 wt. % of a soap surfactant by weight of the soap bar, wherein the soap surfactant is selected from the group consisting of alkali or alkaline earth metal, and ammonium salts of $C_6$-$C_{18}$ carboxylic acids; from 1.5 wt. % to 30 wt. % of a synthetic surfactant by weight of the soap bar, wherein the synthetic surfactant is selected from the group consisting of an anionic surfactant, a nonionic surfactant, and mixtures thereof; from 0.01 wt. % to 2 wt. % of a fragrance component by weight of the soap bar, wherein the fragrance component comprises ketone and/or aldehyde fragrance components; from 0.01 wt. % to 5 wt. % of an amine component by weight of the soap bar, wherein the amine component is selected from the group consisting of a primary amine, a secondary amine, a tertiary amine, a substituted or unsubstituted 2-pyridinol N-oxide material, an amphoteric surfactant, and mixtures thereof; preferably wherein the amphoteric surfactant is selected from the group consisting of an amphoacetate, an amphodiacetate, a betaine, and mixtures thereof; from 0.01 wt. % to 0.5 wt. % of an antioxidant salt by weight of the soap bar, wherein the anti-oxidant salt is selected from the group consisting of an alkali metal metabisulfite, an alkali metal sulfite, an alkali metal bisulfite and mixtures thereof; and wherein the transparent soap bar has a percent transmittance (% T) value of greater than 40% as measured using the method of Measurement of % Transmittance as disclosed herein.

Soap Surfactant

The transparent soap bar for cleaning the skin comprises from 10 wt. % to 30 wt. % of a soap surfactant by weight of the soap bar, preferably from 12 wt. % to 25 wt. % of a soap surfactant by weight of the soap bar, more preferably from 13 wt. % to 22 wt. % of a soap surfactant by weight of the soap bar, even more preferably from 15 wt. % to 20 wt. % of a soap surfactant by weight of the soap bar.

The soap surfactant is selected from the group consisting of alkali or alkaline earth metal, and ammonium salts of $C_6$-$C_{18}$ carboxylic acids.

Sodium, magnesium, potassium, calcium, mono-, di- and tri-ethanol ammonium cations, or combinations thereof, are suitable for purposes of the present invention. In general, sodium soap surfactants are used in the compositions of this invention, but from 1 wt. % to 5 wt. % of the soap may be ammonium, potassium, magnesium, calcium or a mixture of the soap surfactants.

The soap surfactant may comprise alkali or alkaline earth metal of $C_6$-$C_{18}$ carboxylic acids, preferably alkali or alkaline earth metal of $C_{12}$-$C_{18}$ carboxylic acids.

Preferably, the soap surfactant may comprise sodium metal of $C_6$-$C_{18}$ is carboxylic acids, wherein the $C_6$-$C_{18}$ carboxylic acid is selected from the group consisting of caproic acid, caprylic acid, capric acid, lauric acid, myristic acid, palmitic acid, margaric acid, stearic acid, myristoleic acid, palmitoleic acid, sapienic acid, oleic acid, elaidic acid, vaccenic acid, linoleic acid, linoelaidic acid, α-linolenic acid, and combinations thereof.

More preferably, the soap surfactant may comprise sodium metal of $C_6$-$C_{18}$ carboxylic acids, wherein the $C_6$-$C_{18}$ carboxylic acid is selected from the group consisting of caproic acid, caprylic acid, capric acid, lauric acid, myristic acid, palmitic acid, margaric acid, stearic acid, and combinations thereof.

Even more preferably, the soap surfactant may comprise a mixture of stearic acid, palmitic acid and lauric acid; and/or sodium salts thereof.

Most preferred, the soap surfactant may comprise from 15 wt. % to 20 wt. % of a soap surfactant by weight of the soap bar, wherein the soap surfactant comprises a mixture of stearic acid, palmitic acid and lauric acid; and/or sodium salts thereof.

Synthetic Surfactant

Synthetic surfactants can be used in the present transparent soap bars to further improve the lathering properties of the soap bar during use.

Synthetic surfactants are typically incorporated in the transparent soap bar at a level from 1.5 wt. % to 30 wt. % of a synthetic surfactant by weight of the soap bar, preferably from 5 wt. % to 25 wt. % of a synthetic surfactant by weight of the soap bar, more preferably from 7.5 wt. % to 22 wt. % of a synthetic surfactant by weight of the soap bar, even more preferably from 10 wt. % to 20 wt. % of a synthetic surfactant by weight of the soap bar.

The synthetic surfactant is selected from the group consisting of an anionic surfactant, a nonionic surfactant, and mixtures thereof.

Examples of anionic surfactants include but are not limited to alkyl sulfates, anionic acyl sarcosinates, methyl acyl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and the like. Alkyl chains for these surfactants are C8-22, preferably C10-18 and, more preferably, C12-14 alkyls.

Preferably, the anionic surfactant may be selected from the group consisting of: sodium $C_{8-18}$ alkyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_8$-$C_{18}$ alkyl aminopropionate, sodium laureth-1 sulfate, ammonium laureth-1 sulfate, triethanolamine laureth-1 sulfate, sodium tridecyl benzene sulfonate, sodium dodecyl benzene sulfonate, sodium lauroyl sarcosinate, sodium lauroyl sarcosinate, sodium cocoyl sarcosinate, sodium lauroyl methyl isethionate, sodium lauroyl isethionate, sodium cocoyl isethionate, sodium lauroyl glycinate, sodium cocoyl glycinate, potassium lauroyl glycinate, potassium cocoyl glycinate, sodium lauroyl glutamate, potassium lauroyl glutamate, sodium cocoyl glutamate, potassium cocoyl glutamate, disodium lauroyl glutamate, dipotassium lauroyl glutamate, disodium cocoyl glutamate, dipotassium cocoyl glutamate, sodium lauroyl lactylate and mixtures thereof.

More preferably, the anionic surfactant may comprise sodium laureth(n) sulfate SLEnS, wherein n is the average moles of ethoxylation, wherein n ranges from 0 to 8, preferably wherein n ranges from 1 to 3.

It is understood that a material such as SLEnS, for example, can comprise a significant amount of molecules which have no ethoxylate, 1 mole ethoxylate, 2 mole ethoxylate, 3 mole ethoxylate, and so on in a distribution which can be broad, narrow or truncated. For example, SLE1S can comprise a significant amount of molecules which have no ethoxylate, 1 mole ethoxylate, 3 mole ethoxylate, and so on in a distribution which can be broad, narrow or truncated and still comprise SLE1S where the average of the distribution is 1.

The transparent soap bar may comprise from 0.5 wt. % to 15 wt. %, preferably from 5 wt. % to 12 wt. %, more preferably from 8 wt. % to 10 wt. % of an anionic surfactant by weight of the soap bar.

Nonionic surfactants useful in this invention can be broadly defined as compounds produced by the condensation of alkylene oxide groups (hydrophilic in nature) with an organic hydrophobic compound, which may be aliphatic or alkyl aromatic in nature.

The nonionic surfactant may be selected from the group consisting of glucosides, alkyl amines, alcohol ethoxylates, alkyl polyglucosides, alkyl glucosides, acyl glutamide, polyoxyethylene alkyl ether carboxylic acid and mixtures thereof.

Alternatively, the nonionic surfactant may be selected form the group consisting of $C_8$-$C_{14}$ glucose amides, $C_8$-$C_{14}$ alkyl polyglucosides, sucrose cocoate, sucrose laurate, alkanolamides, ethoxylated alcohols and mixtures thereof.

The nonionic surfactant may be preferably selected from the group consisting of glyceryl monohydroxystearate, steareth-2, isosteareth-2, hydroxy stearic acid, propylene glycol stearate, PEG-2 stearate, sorbitan monostearate, glyceryl stearate, glyceryl laurate, laureth-2, cocamide monoethanolamine, lauramide monoethanolamine, and mixtures thereof.

Alternatively, the nonionic surfactant may be selected from cocoamide monoethanolamine, lauramide monoethanolamine, cocoyl glucoside, lauroyl glucoside, decyl glucoside, and mixtures thereof.

Alternatively, the nonionic surfactant may preferably be a polyoxyethylene alkyl ether carboxylic acid. Suitable polyoxyethylene alkyl ether carboxylic acid include, but are not limited to, the following representatives referred to by their INCI names (INCI: nomenclature for raw materials according to the International Cosmetic Ingredient Dictionary, 7$^{th}$ Edition, published by the Cosmetic, Toiletry and Fragrance Association Inc. (CTFA), Washington D.C., USA): Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, $C_{9-11}$ Pareth-6 Carboxylic Acid, $C_{11-15}$ Pareth-7 Carboxylic Acid, $C_{12-13}$ Pareth-5 Carboxylic Acid, $C_{12-13}$ Pareth-8 Carboxylic Acid, $C_{12-13}$ Pareth-12 Carboxylic Acid, $C_{12-15}$ Pareth-7 Carboxylic Acid, $C_{12-15}$ Pareth-8 Carboxylic Acid, $C_{14-15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof.

The nonionic surfactant may be preferably selected from the group consisting of, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, and mixtures thereof, preferably Laureth-6 Carboxylic Acid.

The transparent soap bar may comprise from 1 wt. % to 10 wt. % of a nonionic surfactant, preferably from 3 wt. % to 9 wt. % of a nonionic surfactant, more preferably from 5 wt. % to 9 wt. % of a nonionic surfactant by total weight of the soap bar.

A preferred synthetic surfactant for use in the present soap bars may comprise sodium laureth(n) sulfate SLEnS, wherein n is the average moles of ethoxylation, wherein n ranges from 0 to 8, preferably wherein n ranges from 1 to 3. Sodium laureth(n) sulfate SLEnS, wherein n is the average moles of ethoxylation, wherein n ranges from 0 to 8, preferably wherein n ranges from 1 to 3 tends to provide excellent lathering properties, especially when combined with sodium tripolyphosphate as the inorganic salt in the present compositions.

Alternatively, a preferred synthetic surfactant may be a combination of sodium laureth(n) sulfate SLEnS, wherein n is the average moles of ethoxylation, wherein n ranges from 1 to 3; and laureth-6 carboxylic acid.

Fragrance Component

The transparent soap bar comprises from 0.01 wt. % to 2 wt. % of a fragrance component by weight of the soap bar, preferably from 0.1 wt. % to 1.75 wt. % of a fragrance component by weight of the soap bar, more preferably from 0.5 wt. % to 1.6 wt. % of a fragrance component by weight of the soap bar, even more preferably from 0.8 wt. % to 1.5 wt. % of a fragrance component by weight of the soap bar.

Typically the fragrance component may be a blend of perfumes and aroma chemicals. As used herein, "fragrance" is used to indicate any odoriferous material.

A wide variety of chemicals are known as fragrances, including alcohols, aldehydes, ketones, and esters. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of 500° C. or lower, 400° C. or lower, or 350° C. or lower. The BP of many fragrances are disclosed in *Perfume and Flavor Chemicals* (Aroma Chemicals), Steffen Arctander (1969). The ClogP value of the fragrances may be 0.1 or greater, 0.5 or greater, 1.0 or greater, and 1.2 or greater. As used herein, "ClogP" means the logarithm to the base 10 of the octanol/water partition coefficient. The ClogP may be readily calculated from a program called "CLOGP" which is available from Daylight Chemical Information Systems Inc., Irvine Calif., USA. Octanol/water partition coefficients are described in more detail in U.S. Pat. No. 5,578,563.

Suitable fragrances are also disclosed in U.S. Pat. Nos. 4,145,184, 4,209,417, 4,515,705, and 4,152,272. Non-limiting examples of fragrances include animal fragrances such as musk oil, civet, castoreurn, ambergris, plant fragrances such as nutmeg extract, cardomon extract, ginger extract, cinnamon extract, patchouli oil, geranium oil, orange oil, mandarin oil, orange Hower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomile oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof.

Other examples of suitable fragrances include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-bexenyl methyl carbonate, citral, citronellol and ester derivatives, cumin aldehyde, cyclamen aldehyde, cyclogalbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltoiide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dibydrojasmonate, methyl eugenol, methyl ionone, methyl-α-naphthyl ketone, methylphenylcarbinyl acetate, mugetanol, γ-nonalactone, octanal, phenyl ethyl acetate, phenylacetaldehyde dimethyl acetate, phenoxyethyl isobutyrate, phenyl ethyl alcohol, pinenes, sandalore, santaiol, stemone, thymol, terpenes, triplal, triethyl citrate, 3,3,5-trimethylcyclohexanol, γ-undecalactone, undecenal, vanillin, veloutone, verdox, and mixtures thereof.

In the transparent soap bar, the fragrance component comprises ketone and/or aldehyde fragrance components. In addition, the fragrance component may further comprise any fragrances as set out just above.

Ketone fragrance components may be selected from alicyclic ketones such a β-ionone, terpene ketones such as 1-carvone, and macrocyclic ketones such as cyclopentadecanone.

Aldehyde fragrance components may be selected from fatty aldehydes such as 2,6-nonadienal, terpene aldehydes such as citral, and aromatic aldehydes such as α-hexylcinnamic aldehyde, cinnamaldehyde.

Thus, preferably the fragrance component may comprise ketone and/or aldehyde fragrance components, wherein the ketone and/or aldehyde fragrance components may be selected from the group consisting of acetophenone, adoxal, aldehyde C-12, aldehyde C-14, aldehyde C-18, α-amylcinnamic aldehyde, anisaldehyde, benzaldehyde, camphor, cinnamaldehyde, citral, cumin aldehyde, cyclamen aldehyde, damascones, fenchone, helional, 2-heptonone, α-hexylcinnamic aldehyde, hydroxycitrolnellal, ionones, lilial, lyral, melonal, p-methylacetophenone, methyl cedrylone, methyl ionone, methyl-α-naphthyl ketone, γ-nonalactone, octanal, phenylacetaldehyde dimethyl acetate, triplal, γ-undecalactone, undecenal, vanillin, veloutone, and mixtures thereof.

Amine Component

The transparent soap bar comprises from 0.01 wt. % to 5 wt. % of an amine component by weight of the soap bar, preferably from 0.2 wt. % to 5 wt. % of an amine component by weight of the soap bar, more preferably from 0.5 wt. % to 3.5 wt. % of an amine component by weight of the soap bar, even more preferably from 0.7 wt. % to 2.5 wt. % of an amine component by weight of the soap bar.

The amine component is selected from the group consisting of a primary amine, a secondary amine, a tertiary amine, a substituted or unsubstituted 2-pyridinol N-oxide material, an amphoteric surfactant, and mixtures thereof.

Preferably, the amphoteric surfactant may be selected from the group consisting of an amphoacetate, an amphodiacetate, a betaine, and mixtures thereof.

Simple Primary, Secondary, and Tertiary Amines

A primary amine may a mono $C_{1-4}$ alkyl amine or a mono $C_{1-4}$ alkanol amine. The mono $C_{1-4}$ alkyl amine may be methylamine, ethylamine, isopropylamine, propylamine, tertiobutylamine or butylamine.

The mono $C_{1-4}$ alkanol amine may be ethanolamine, isopropanolamine, propanolamine, or butanolamine.

A secondary amine may a di $C_{1-4}$ alkyl amine or a di $C_{1-4}$ alkanol amine. The di $C_{1-4}$ alkyl amine may be dimethylamine, diethylamine, diisopropylamine, dipropylamine, ditertiobutylamine or dibutylamine.

The di $C_{1-4}$ alkanol amine may be diethanolamine, diisopropanolamine, dipropanolamine, or dibutanolamine.

A tertiary amine may a tri $C_{1-4}$ alkyl amine or a tri $C_{1-4}$ alkanol amine. The tri $C_{1-4}$ alkyl amine may be trimethylamine, triethylamine, triisopropylamine, tripropylamine, tritertiobutylamine or tributylamine.

The tri $C_{1-4}$ alkanol amine may be trimethanolamine, triethanolamine, triisopropanolamine, tripropanolamine, or tributanolamine.

2-pyridinol-N-oxide Material

The amine component may comprise a substituted or unsubstituted 2-pyridinol N-oxide material or a salt thereof.

The substituted or unsubstituted 2-pyridinol-N-oxide material or a salt thereof and its corresponding tautomeric form, 1-hydroxy-2(1H)-pyridinone, are shown below:

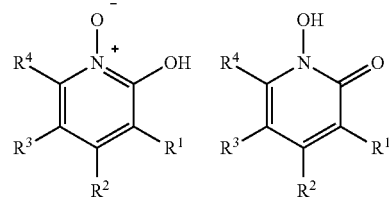

where $R^1$, $R^2$, $R^3$, $R^4$ groups are independently selected from the group consisting of H, Cl, Br, I, F, NO, $NO_2$, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $^+N(R^7R^8R^9R^{10})$, and 1/q M' $^{q+}$ where M' is selected from the group consisting of an alkali metal of charge q and an alkaline earth metal of charge q, where $R^7$, $R^8$, $R^9$, and $R^{10}$ are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

The substituted or unsubstituted 2-pyridinol-N-oxide material may be a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1.

The substituted or unsubstituted 2-pyridinol-N-oxide material may be a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

The 2-pyridinol-N-oxide material may be the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, ½ $Mg^{2+}$, or ½ $Ca^{2+}$, substituted ammonium, such as $C_1$-$C_6$ alkanolammnonium, mono-ethanolamine (MEA), tri-ethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

The 2-pyridinol-N-oxide material may be of a substituted or unsubstituted 2-pyridinol-N-oxide material. Salts for use herein include those formed from the polyvalent metals barium, bismuth, strontium, copper, zinc, cadmium, zirconium and mixtures thereof.

The 2-pyridinol-N-oxide material may be selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available, for example, Sigma-Aldrich (St. Louis, MO) and/or Aces Pharma (Branford, CT).

The 2-pyridinol-N-oxide material may be a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

The 2-pyridinol-N-oxide material may be a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, MO), Princeton Building Blocks (Monmouth Junction, NJ), 3B Scientific Corporation (Libertyville, IL), SynFine Research (Richmond Hill, ON), Ryan Scientific, Inc. (Mt. Pleasant, SC), and/or Aces Pharma (Branford, CT).

The 2-pyridinol-N-oxide material may be a 2-pyridinol-N-oxide material or tautomer thereof according to the formula(s) below:

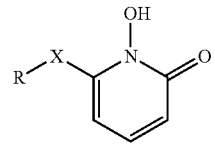

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

The 2-pyridinol-N-oxide material may be a 2-pyridinol-N-oxide material or tautomer thereof according to the formula(s) below:

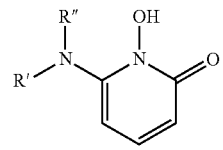

wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013.

Preferably, the substituted or unsubstituted 2-pyridinol-N-oxide material may be 1-hydroxy-4-methyl-6-(2,4,4-trimethylpentyl)-2-pyridone monoethanolamine salt, also named 1-hydroxy-4-methyl-6-(2,4,4-trimethylpentyl)-2-(1H)pyridinone 2-aminoethanol salt, or piroctone olamine Amphoteric Surfactant The amine component may comprise an amphoteric surfactant. Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from 8 to 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate; N-alkyltaurines, such as the one prepared by reacting dodecylamine with sodium isethionate according to the teaching of U.S. Pat. No. 2,658,072; N-higher alkyl aspartic acids, such as those produced according to the teaching of U.S. Pat. No. 2,438,091; and the products sold under the trade name "Miranol" and described in U.S. Pat. No. 2,528,378.

The amphoteric surfactant may be selected from the group consisting of an amphoacetate, an amphodiacetate, a betaine, and mixtures thereof.

Amphoacetates and amphodiacetates may be used.
Amphoacetate:

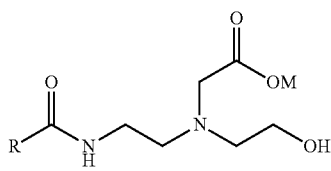

Amphodiacetate:

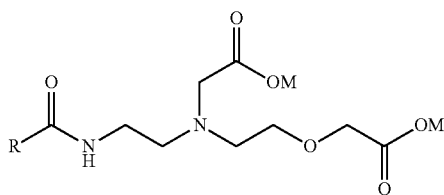

Amphoacetates and amphodiacetates conform to the formulas (above) where R may be an aliphatic group of 8 to 18 carbon atoms. M may be a cation such as sodium, potassium, ammonium, or substituted ammonium.

The amphoteric surfactant may be selected from the group consisting of sodium lauroamphoacetate, sodium cocoamphoacetate, disodium lauroamphoacetate, disodium cocoamphodiacetate, and mixtures thereof.

An amphoacetate or amphodiacetate can help for boosting the lather and foaming properties of the transparent soap bar.

Alternatively, the amphoteric surfactant may comprise a betaine. A betaine can help for boosting the lather and foaming properties of the transparent soap bar as an alternative of the amphoacetate or amphodiacetate.

Amphoteric surfactants such as betaines that useful in the present composition may include the high alkyl betaines such as coco dimethyl carboxymethyl betaine, coco-betaine, oleyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyethyl betaine, and mixtures thereof.

The sulfobetaines may be represented by coco dimethyl sulfopropyl betaine, stearyl dimethyl sulfopropyl betaine, amido betaines, amidosulfobetaines, and the like.

More preferably, the betaine may be selected from the group consisting of cocamidopropyl betaine, lauramidopropyl betaine and mixtures thereof. Even more preferably, the betaine may comprise cocamidopropyl betaine.

Alternatively, the amphoteric surfactant may be selected from the group consisting of sodium lauroamphoacetate, sodium cocoamphoacetate, disodium lauroamphoacetate, disodium cocoamphodiacetate, cocamidopropyl betaine, lauramidopropyl betaine, and mixtures thereof. Preferably, the amphoteric surfactant may be selected from the group consisting of cocamidopropyl betaine, sodium lauroamphoacetate, and mixtures thereof.

Alternatively the amine component may be selected from the group consisting of ethanolamine, diethanolamine, triethanolamine, cocamidopropyl betaine, lauramidopropyl betaine, cocamidopropyl hydroxysultaine, lauramidopropyl hydroxysultaine, sodium lauroamphoacetate, piroctone olamine and mixtures thereof.

Most preferably, the amine component may comprise a mixture of cocamidopropyl betaine and piroctone olamine; or comprise a mixture of sodium lauroamphoacetate and piroctone olamine Antioxidant Salt The transparent soap bar comprises from 0.01 wt. % to 0.5 wt. % of an antioxidant salt by weight of the soap bar, preferably from 0.05 wt. % to 0.4 wt. % of an antioxidant salt by weight of the soap bar, more preferably from 0.10 wt. % to 0.3 wt. % of an antioxidant salt by weight of the soap bar, even more preferably from 0.15 wt. % to 0.3 wt. % of an antioxidant salt by weight of the soap bar.

The anti-oxidant salt is selected from the group consisting of an alkali metal metabisulfite, an alkali metal sulfite, an alkali metal bisulfite and mixtures thereof.

The alkali metal in the antioxidant salt may be sodium or potassium, preferably sodium.

Preferably, the anti-oxidant salt may be selected from the group consisting sodium metabisulfite, sodium sulfite, potassium sulfite, sodium bisulfite, potassium bisulfite and mixtures thereof. More preferably, the anti-oxidant salt may be selected from the group consisting sodium bisulfite, potassium bisulfite and mixtures thereof. Most preferred, the anti-oxidant salt may comprise sodium bisulfite.

The addition of specific antioxidant salt can prevent any discoloration due to the unwanted reaction between the amine component and the aldehyde and/or ketone fragrance components.

As shown in the experimental part, the discoloration prevention or reduction could be assessed by measuring the spectrophotometric parameters for overall color change ΔE. The discoloration prevention or reduction of the transparent soap bar has been evidenced by the reduction of ΔE when adding of an antioxidant salt as recited hereinbefore.

The overall color is also defined with a (red/green values), b (yellow/blue values) and L (lightness) values in the Hunter L a b scale. Thus a decrease of one single color component, e.g. yellowing might not sufficient to assert that the discoloration has been prevented or reduced. The total color difference needs to be measured and it is expressed as:

$$\Delta E = ((L_1 - L_2)^2 + (a_1 - a_2)^2 + (b_1 - b_2)^2)^{1/2}$$

Wherein $L_1$, $a_1$, $b_1$ are the values for the fresh made soap bar ("initial"); $L_2$, $a_2$, $b_2$ are the values for the aged soap bar ("final").

Humectant

The transparent soap bar may comprise a humectant, wherein the humectant is selected from the group consisting of glycerin, propylene glycol, 1,2-butylene glycol, 1,3-butylene glycol, 1,4-butylene glycol, decylene glycol, polyethylene glycol, sorbitol, sucrose and mixtures thereof. The humectants are also known as conventional transparent or clarifying agents.

The transparent soap bar may comprise from 20 wt. % to 60 wt. % of a humectant by weight of the soap bar, preferably from 22 wt. % to 50 wt. % of a humectant by weight of the soap bar, more preferably from 23 wt. % to 40 wt. % of a humectant by weight of the soap bar, even more preferably from 25 wt. % to 30 wt. % of a humectant by weight of the soap bar.

Other Ingredients

The transparent soap bar may include a zwitterionic surfactant. Zwitterionic surfactant may be exemplified by those which can be broadly described as derivatives of aliphatic quaternary ammonium, phosphonium, and sulfonium compounds, in which the aliphatic radicals can be straight chain or branched and wherein one of the aliphatic substituents contains from 8 to 18 carbon atoms and one contains an anionic water-solubilizing group, for example, carboxy, sulfonate, sulfate, phosphate, or phosphonate. Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3-dodecoxy-2-hydroxypropylammonio]-propane-1-phosphonate; 3-(N,N-di-methyl-N-hexadecylammonio)propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

The transparent soap bar may comprise from 0.01% to 2.5% of the zwitterionic surfactant by weight of the cleansing bar, preferably from 0.1% to 2.4% of the zwitterionic surfactant by weight of the cleansing bar, more preferably from 0.3% to 2.3% of the zwitterionic surfactant by weight of the cleansing bar, even more preferably from 0.5% to 2.0% of the zwitterionic surfactant by weight of the cleansing bar.

The transparent soap bar may comprise other ingredients such as an emollient and a chelating agent.

The emollient may comprise mineral oil, vegetable oil, silicone oils, synthetic and semisynthetic emollient esters and mixtures thereof. The emollient can help to provide to the user's skin with a soft, silky feeling after using the soap bar.

The chelating agent can complex any relatively heavy metal ions that could catalyze any reactions contributing to the discoloration of the soap bar. The chelating agent may comprise the tetrasodium salt of ethylenediamine tetraacetic acid (EDTA), and the pentasodium salt of diethylenetriamine pentaacetic acid ($Na_5DTPA$).

METHOD OF MANUFACTURE, PRODUCT FORMS AND USES

Method of Manufacture and Product Forms

Most preferred, the transparent soap bar may be typically made through a melt and pour manufacturing process.

In the first step, the soap chassis is made via the following steps, preferably in that order: C6-C18 carboxylic acids such as lauric acid, stearic acid, palmitic acid, synthetic surfactants like SLEnS, and any humectants such as glycols (propylene glycol, butylene glycol and glycerin) are mixed with a sodium hydroxide solution in a container at 70-90° C., preferably at 75° C. for 4-8 hours to fully convert the carboxylic acids to the sodium metal carboxylic acids making the soap surfactants.

Once fully reacted, other humectants, such as sucrose and sorbitol, may be added to the melt mixture and mixed for 10 minutes. The melt mixture is sonicated for 10 seconds for degassing the melt mixture to lead to the soap chassis.

The melt mixture is then be poured into a mold to form the solid soap chassis. If needed, the soap chassis may be remelted at 75° C. for 1 h.

The amine component (e.g. piroctone olamine, triethanolamine, or cocamidopropyl betaine) is added in the melt mixture of the soap chassis and mixed for 10 mins for complete dissolution. Afterwards, the fragrance component (perfume, or cinnamaldehyde) and the antioxidant salt in solution, e.g. sodium bisulfite when needed are added and mixed for 2 minutes. The melt mixture is degassed and poured into a mold. After cooling the mold to room temperature, the transparent soap bar is fully solidified and can be cut into the desired final product form.

The product form of the transparent soap bar may include a round, oval, elliptic, parallelepiped shape, i.e. a hexahedron shape of the soap bar.

The transparent soap bar may have a narrow centered portion. The narrow centered portion of the soap bar may be defined as the centered region of the soap bar extending along a longitudinal axis of the soap bar and having a relatively narrow width as measured in the transversal direction perpendicular to the longitudinal axis.

Alternatively, the transparent soap bar may be typically made through conventional roll-milling/plodding manufacturing process.

Methods of Use

The antioxidant salt can be used for preventing or reducing any discoloration of the transparent soap bar. Preferably, the antioxidant salt can be used for preventing or reducing any yellowing discoloration of the transparent soap bar.

The anti-oxidant salt is selected from the group consisting of an alkali metal metabisulfite, an alkali metal sulfite, an alkali metal bisulfite and mixtures thereof.

A method for preventing or reducing any discoloration of a transparent soap bar as set out hereinbefore is provided and comprises the steps of, preferably in that order, adding from 0.01 wt. % to 0.5 wt. % of an antioxidant salt by weight of the soap bar, wherein the anti-oxidant salt is selected from the group consisting of an alkali metal metabisulfite, an alkali metal sulfite, an alkali metal bisulfite and mixtures thereof; to a premix comprising: from 10 wt. % to 30 wt. % of a soap surfactant by weight of the soap bar, wherein the soap surfactant is selected from the group consisting of alkali or alkaline earth metal, and ammonium salts of $C_6$-$C_{18}$ carboxylic acids; from 1.5 wt. % to 30 wt. % of a synthetic surfactant by weight of the soap bar, wherein the synthetic surfactant is selected from the group consisting of an anionic surfactant, a nonionic surfactant, and mixtures thereof; from 0.01 wt. % to 2 wt. % of a fragrance component by weight of the soap bar, wherein the fragrance component comprises ketone and/or aldehyde fragrance components; from 0.01 wt. % to 5 wt. % of an amine component by weight of the soap bar, wherein the amine component is selected from the group consisting of a primary amine, a secondary amine, a tertiary amine, a substituted or unsubstituted 2-pyridinol N-oxide material, an amphoteric surfactant, and mixtures thereof; preferably wherein the amphoteric surfactant is selected from the group consisting of an amphoacetate, an amphodiacetate, a betaine, and mixtures thereof; wherein the resulting transparent soap bar has a percent transmittance (% T) value of greater than 40% as measured using the method of Measurement of % Transmittance as disclosed herein.
Transparency The term "clear" or "transparent" as used herein, means that the transparent soap bar have a percent transmittance (% T) of at least 40% transmittance, preferably from 400 nm to 700 nm via light transmission through the sample, as measured using the method of Measurement of % Transmittance as disclosed herein. The % T may be from 45% to 100%, from 50% to 100%, from 55% to 100%, from 60% to 100%, from 75% to 100%, from 80% to 100%, from 85% to 100%, from 90% to 100%, from 95% to 100%.

The transparency of the transparent soap bar is measured by a benchtop spectrophotometer, which determines the absorption or transmission of UV/VIS light through a sample, using an X-rite Ci 7800 instrument according to the related instructions. A light wavelength from 400 nm to 700 nm has been shown to be adequate for characterizing the degree of clarity of the transparent soap bars.

TEST METHODS

It is understood that the test methods that are disclosed in the Test Methods Section of the present application should be used to determine the respective values of the parameters of Applicants' invention as such invention is described and claimed herein.

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. All tests are conducted under the same environmental conditions and in such conditioned room. All instruments are calibrated according to manufacturer's specifications.
Measurement of % Transmittance (% T)

Techniques for analysis of the clarity or transparency of a soap bar are typically based on the use of a spectrophotometer to measure the percent transmittance (% T) through the sample (% T).

The percent transmittance (% T) can be measured using a benchtop spectrophotometer X-rite Ci 7800 instrument which determines the transmission of UV/VIS light through a sample. A light wavelength from 400 nm to 700 nm has been shown to be adequate for characterizing the degree of light transmittance through a sample. Typically, it is best to follow the specific instructions relating to the specific spectrophotometer being used. In general, the procedure for measuring percent transmittance starts by setting the spectrophotometer from 400 nm to 700 nm. Then a calibration "blank" is run to calibrate the readout to 100 percent transmittance.

A single soap bar test sample with dimension of (62 mm*37 mm*16.5 mm) is placed between two aperture plates within the measurement chamber. The incident light transmits through the transparent bar and the absorbance of the lights was recorded over the wavelength range of 400-700 nm. The percent transmittance (% T) is provided from the resultant color spectrum.
Color Variation Test Method The color variation test method was the key method to monitor soap color stability and to assess whether discoloration has been prevented or reduced. In the color variation test method, the transparent soap bars were stamped into dimension of (62 mm*37 mm*16.5 mm). The color of the soap bar to be tested was evaluated using a benchtop spectrophotometer (a X-rite Ci 7800 instrument) via transmission mode. The soap bar to be tested was placed between 2 aperture plates within the measurement chamber. The incident light transmits through the soap bar to be tested and the absorbance of the lights was recorded over the wavelength range of 300-800 nm. The resulting curve was converted to the various color scale, L, a and b values.

L represents the lightness of the color, a indicates the green/red color axis and b the blue/yellow color axis.

Analysis of color was based on individual color components in the Hunter L a b color space, wherein:
L=lightness (L=0 yields black and L=100 indicates diffuse white)
a=red/green (a, negative values indicate green while positive values indicate red)
b=yellow to blue (b, negative values indicate blue and positive values indicate yellow)

To evaluate the color stability of the soap bar, soap color was measured when it is freshly made and after being aged at 75° C. for 4 hours.

Given ΔL Δa Δb, the total difference or distance with Hunter L a b scale can be stated as a single value, known as ΔE.

$$\Delta E = ((L_1-L_2)^2 + (a_1-a_2)^2 + (b_1-b_2)^2)^{1/2}$$

wherein
$L_1$, $a_1$, $b_1$ are the values for the fresh made soap bar ("initial"); $L_2$, $a_2$, $b_2$ are the values for the aged soap bar ("final").

A higher ΔE value indicates larger color shift from initial value, which is unfavorable meaning that more color has been formed within the soap bar.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The following chassis to be used in the examples is provided below:
Composition (% wt.)

| Components | Soap chassis |
|---|---|
| Lauric acid*[1] | 4.8% |
| Glycerin*[2] | 4.4% |
| Propylene glycol*[3] | 7.1% |
| 1,3-butylene glycol*[4] | 5.3% |
| Stearic acid*[5] | 6.2% |
| Palmitic acid*[6] | 8.8% |
| Sucrose*[7] | 15.0% |
| Sorbitol*[8] | 13.2% |
| Sodium laureth(3) sulfate (SLE3S) *[9] | 8.1% |
| Sodium hydroxide*[10] | 3.3% |
| Disodium EDTA*[11] | 0.05% |
| Water | qsp |
| Total | 100.00% |

The following soap bars Ex. 1-14 comprising a perfume and/or an amine component (piroctone olamine, or triethanolamine, or cocamidopropyl betaine) were prepared and assessed in terms of color stability and transparency when having or not an antioxidant salt such as sodium bisulfite. Compositions (% wt.)

In terms of % Transmittance, the clarity of the transparent soap bars were improved for Ex. 6 and Ex. 10 when adding the antioxidant salt and the clarity was still acceptable for Ex. 14.

| Components, wt. % | CEx. 1 | CEx. 2 | CEx. 3 | CEx. 4 | CEx. 5 | Ex. 6 |
|---|---|---|---|---|---|---|
| Soap chassis | 99.3% | 98.55 | 98.8% | 98.05% | 98.1% | 97.35% |
| Piroctone olamine*[12] | 0.7% | 0.7% | — | — | 0.7% | 0.7% |
| Perfume | — | — | 1.2% | 1.2% | 1.2% | 1.2% |
| Sodium bisulfite*[13] (40 wt. % active) | — | 0.75% (0.3%) | — | 0.75% (0.3%) | — | 0.75% (0.3%) |
| Total | 100% | 100% | 100% | 100% | 100% | 100% |
| % Transmittance (% T) | 44.5% | 54.2% | 48.1% | 52.6% | 43.7% | 75.1% |
| $L_1$ value (initial) | 69.0 | 76.2 | 71.5 | 74.9 | 67.8 | 90.0 |
| $a_1$ value (initial) | 1.0 | −0.2 | 1.3 | 0.6 | 1.1 | −2.1 |
| $b_1$ value (initial) | 20.1 | 18.8 | 18.4 | 17.9 | 19.6 | 13.4 |
| $L_2$ value (final) | 71.7 | 81.3 | 75.4 | 84.7 | 72.6 | 87.7 |
| $a_2$ value (final) | 0.6 | −1.1 | 0.4 | −0.8 | −0.1 | −2.2 |
| $b_2$ value (final) | 20.4 | 17.5 | 17.7 | 12.9 | 19.1 | 13.0 |
| $\Delta E$ | 2.7 | 5.3 | 4.1 | 11.1 | 4.9 | 2.3 |

| Components, wt. % | CEx. 7 | CEx. 8 | CEx. 3 | CEx. 4 | CEx. 9 | Ex. 10 |
|---|---|---|---|---|---|---|
| Soap chassis | 99.5% | 98.75% | 98.8% | 98.05% | 98.3% | 97.55% |
| Triethanolamine*[14] | 0.5% | 0.5% | — | — | 0.5% | 0.5% |
| Perfume | — | — | 1.2% | 1.2% | 1.2% | 1.2% |
| Sodium bisulfite*[13] (40 wt. % active) | — | 0.75% (0.3%) | — | 0.75% (0.3%) | — | 0.75% (0.3%) |
| Total | 100% | 100% | 100% | 100% | 100% | 100% |
| % Transmittance (% T) | 55.6% | 51.1% | 48.1% | 52.6% | 55.9% | 59.3% |
| $L_1$ value (initial) | 76.5 | 74.1 | 71.5 | 74.9 | 77.1 | 79.7 |
| $a_1$ value (initial) | 0.6 | 0.4 | 1.3 | 0.6 | 0.1 | −0.3 |
| $b_1$ value (initial) | 17.1 | 17.8 | 18.4 | 17.9 | 17.1 | 17.3 |
| $L_2$ value (final) | 75.9 | 74.1 | 75.4 | 84.7 | 75.8 | 81.8 |
| $a_2$ value (final) | 0.6 | 0.4 | 0.4 | −0.8 | 0.4 | −0.8 |
| $b_2$ value (final) | 17.4 | 17.7 | 17.7 | 12.9 | 19.2 | 16.4 |
| $\Delta E$ | 0.7 | 0.1 | 4.1 | 11.1 | 2.5 | 2.4 |

| Components, wt. % | CEx. 11 | CEx. 12 | CEx. 3 | CEx. 4 | CEx. 13 | Ex. 14 |
|---|---|---|---|---|---|---|
| Soap chassis | 98.3% | 97.55% | 98.8% | 98.05% | 97.1% | 96.35% |
| Coamidopropyl betaine (30 wt. % active)*[15] | 1.7% (0.5%) | 1.7% (0.5%) | — | — | 1.7% (0.5%) | 1.7% (0.5%) |
| Perfume | — | — | 1.2% | 1.2% | 1.2% | 1.2% |
| Sodium bisulfite*[13] (40 wt. % active) | — | 0.75% (0.3%) | — | 0.75% (0.3%) | — | 0.75% (0.3%) |
| Total | 100% | 100% | 100% | 100% | 100% | 100% |
| % Transmittance (% T) | 51.5% | 56.3% | 48.1% | 52.6% | 57.9% | 56.5% |
| $L_1$ value (initial) | 73.9 | 77.4 | 71.5 | 74.9 | 78.1 | 77.7 |
| $a_1$ value (initial) | 0.6 | 0.0 | 1.3 | 0.6 | 0.3 | −0.5 |
| $b_1$ value (initial) | 17.8 | 17.5 | 18.4 | 17.9 | 16.5 | 18.2 |
| $L_2$ value (final) | 73.7 | 73.8 | 75.4 | 84.7 | 72.7 | 76.8 |
| $a_2$ value (final) | 0.5 | 0.6 | 0.4 | −0.8 | 1.1 | −0.4 |
| $b_2$ value (final) | 17.3 | 18.7 | 17.7 | 12.9 | 19.6 | 19.0 |
| $\Delta E$ | 0.6 | 3.9 | 4.1 | 11.1 | 6.2 | 1.2 |

Colorimetric and Transmittance Results

When the soap bar comprises a mixture of an amine component such as piroctone olamine, or triethanolamine, or cocamidopropyl betaine with a fragrance component comprising ketone and/or aldehyde components, the addition of an antioxidant salt such as sodium bisulfite has decreased the $\Delta E$ value showing that the discoloration of the transparent soap bar has been prevented or reduced.

The following soap bars Ex. 15-22 comprising cinnamaldehyde as a fragrance component and/or an amine component (piroctone olamine, or triethanolamine, or cocamidopropyl betaine) were prepared and assessed in terms of color stability and transparency when having or not an antioxidant salt such as sodium bisulfite.

Compositions (% wt.)

| Components, wt. % | CEx. 1 | CEx. 2 | CEx. 15 | CEx. 16 | CEx. 17 | Ex. 18 |
|---|---|---|---|---|---|---|
| Soap chassis | 99.3% | 98.55 | 99.5% | 98.75% | 98.8% | 98.05% |
| Piroctone olamine*[12] | 0.7% | 0.7% | — | — | 0.7% | 0.7% |
| Cinnamaldehyde*[16] | — | — | 0.5% | 0.5% | 0.5% | 0.5% |
| Sodium bisulfite*[13] | — | 0.75% | — | 0.75% | — | 0.75% |

-continued

| | | (0.3%) | | (0.3%) | | (0.3%) |
|---|---|---|---|---|---|---|
| (40 wt. % active) | | | | | | |
| Total | 100% | 100% | 100% | 100% | 100% | 100% |
| % Transmittance (% T) | 44.5% | 54.2% | 44.8% | 47.4% | 42.9% | 44.4% |
| $L_1$ value (initial) | 69.0 | 76.2 | 70.5 | 73.1 | 69.3 | 70.1 |
| $a_1$ value (initial) | 1.0 | −0.2 | −1.7 | −1.4 | −1.9 | −0.4 |
| $b_1$ value (initial) | 20.1 | 18.8 | 25.7 | 23.6 | 31.2 | 23.7 |
| $L_2$ value (final) | 71.7 | 81.3 | 63.4 | 67.3 | 48.47 | 69.6 |
| $a_2$ value (final) | 0.6 | −1.1 | 6.3 | 0.3 | 24.4 | −0.4 |
| $b_2$ value (final) | 20.4 | 17.5 | 38.5 | 39.2 | 32.2 | 33.6 |
| ΔE | 2.7 | 5.3 | 16.7 | 16.8 | 33.6 | 9.9 |

| Components, wt. % | CEx. 7 | CEx. 8 | CEx. 15 | CEx. 16 | CEx. 19 | Ex. 20 |
|---|---|---|---|---|---|---|
| Soap chassis | 99.5% | 98.75% | 99.5% | 98.75% | 99.0% | 97.55% |
| Triethanolamine*14 | 0.5% | 0.5% | — | — | 0.5% | 0.5% |
| Cinnamaldehyde*16 | — | — | 0.5% | 0.5% | 0.5% | 0.5% |
| Sodium bisulfite*13 | — | 0.75% | — | 0.75% | — | 0.75% |
| (40 wt. % active) | | (0.3%) | | (0.3%) | | (0.3%) |
| Total | 100% | 100% | 100% | 100% | 100% | 100% |
| % Transmittance (% T) | 55.6% | 51.1% | 44.8% | 47.4% | 44.4% | 47.0% |
| $L_1$ value (initial) | 76.5 | 74.1 | 70.5 | 73.1 | 71.6 | 72.1 |
| $a_1$ value (initial) | 0.6 | 0.4 | −1.7 | −1.4 | −2.4 | −2.0 |
| $b_1$ value (initial) | 17.1 | 17.8 | 25.7 | 23.6 | 29.7 | 25.5 |
| $L_2$ value (final) | 75.9 | 74.1 | 63.4 | 67.3 | 55.5 | 66.0 |
| $a_2$ value (final) | 0.6 | 0.4 | 6.3 | 0.3 | 17.7 | 6.5 |
| $b_2$ value (final) | 17.4 | 17.7 | 38.5 | 39.2 | 36.6 | 41.6 |
| ΔE | 0.7 | 0.1 | 16.7 | 16.8 | 26.7 | 19.2 |

| Components, wt. % | CEx. 11 | CEx. 12 | CEx. 15 | CEx. 16 | CEx. 21 | Ex. 22 |
|---|---|---|---|---|---|---|
| Soap chassis | 98.3% | 97.55% | 99.5% | 98.75% | 97.1% | 96.35% |
| Coamidopropyl betaine | 1.7% | 1.7% | — | — | 1.7% | 1.7% |
| (30 wt. % active)*15 | (0.5%) | (0.5%) | | | (0.5%) | (0.5%) |
| Cinnamaldehyde*16 | — | — | 0.5% | 0.5% | 0.5% | 0.5% |
| Sodium bisulfite*13 | — | 0.75% | — | 0.75% | — | 0.75% |
| (40 wt. % active) | | (0.3%) | | (0.3%) | | (0.3%) |
| Total | 100% | 100% | 100% | 100% | 100% | 100% |
| % Transmittance (% T) | 51.5% | 56.3% | 44.8% | 47.4% | 44.0% | 46.5% |
| $L_1$ value (initial) | 73.9 | 77.4 | 70.5 | 73.1 | 70.3 | 71.8 |
| $a_1$ value (initial) | 0.6 | 0.0 | −1.7 | −1.4 | −2.0 | −1.5 |
| $b_1$ value (initial) | 17.8 | 17.5 | 25.7 | 23.6 | 28.4 | 24.7 |
| $L_2$ value (final) | 73.7 | 73.8 | 63.4 | 67.3 | 56.5 | 65.3 |
| $a_2$ value (final) | 0.5 | 0.6 | 6.3 | 0.3 | 15.0 | 6.7 |
| $b_2$ value (final) | 17.3 | 18.7 | 38.5 | 39.2 | 36.8 | 40.8 |
| ΔE | 0.6 | 3.9 | 16.7 | 16.8 | 23.4 | 19.2 |

Colorimetric and Transmittance Results

When the soap bar comprises a mixture of an amine component such as piroctone olamine, or triethanolamine, or cocamidopropyl betaine with a fragrance component being cinnamaldehyde, the addition of an antioxidant salt such as sodium bisulfite has decreased significantly the ΔE value.

Hence, the addition of an antioxidant salt in a transparent soap bar can prevent or reduce discoloration of the transparent soap bar.

In terms of % Transmittance, the clarity of the transparent soap bars were improved for Ex. 18, Ex. 20 and Ex. 22 when adding the antioxidant salt.

Definitions of Components
  *1 Lauric acid from KLK, trade name PALMERA A9912
  *2 Glycerin from P&G, trade name: Superol K
  *3 Propylene glycol from DOW, trade name: Propylene Glycol USP/EP
  *4 1,3-butylene glycol from OXEA Corporation, trade name: 1,3-butylene glycol
  *5 Stearic acid from KLK, trade name: PALMERA A9218
  *6 Palmitic acid from KLK, trade name PALMERA A9816
  *7 sucrose from Sigma Aldrich, trade name BioXtra, S7903
  *8 Sorbitol from Sigma-Aldrich, trade name: D-sorbitol, S1876
  *9 Sodium laureth(3) sulfate (SLE3S) from Guangzhou Litze Chemical Co., Ltd, trade name: SLE3S-28
  *10 sodium hydroxide from Sigma-Aldrich, trade name: S5881
  *11 Disodium EDTA from BASF, trade name: Edeta® BD
  *12 piroctone olamine from Apple Flavor & Fragrance Group, trade name: piroctone olamine
  *13 sodium bisulfate from Suzhou Boyang Chemical, trade name: sodium bisulfite solution
  *14 triethanolamine from DOW, triethanolamine 99%
  *15 cocamidopropyl betaine from TINCI, trade name: Tinci (R) TC-CAB 35H
  *16 cinnamaldehyde from Sigma-Aldrich, trade name: C80687

Method of Preparation

The above soap bars of CEx. 1-5, 7-9, 11-13, 15-17, 19, 21 and Ex. 6, 10, 14, 18, 20, 22 were prepared by the following method:

The transparent soap bars were typically made through a melt and pour manufacturing process. In a first step, the soap chassis was made via the following steps: lauric acid, stearic acid, palmitic acid, synthetic surfactants like SLE3S, and glycols (propylene glycol, butylene glycol and glycerin) were mixed with a sodium hydroxide solution in a metal tank at 75° C. for 4-8 hours to fully convert the carboxylic acids to the sodium metal carboxylic acids making the soap surfactants. Once fully reacted, sucrose, sorbitol were added to the melt mixture and mixed for 10 minutes. The melt mixture was sonicated for 10 seconds for degassing the melt mixture. The melt mixture was then poured into a mold to form the solid soap chassis.

In the second step, the soap chassis may be remelted at 75° C. for 1 hour. Once fully melting, the amine component (piroctone olamine, triethanolamine, or cocamidopropyl betaine) was added and mixed for 10 mins for complete dissolution. Afterwards, the fragrance component (perfume, or cinnamaldehyde) and the antioxidant salt sodium bisulfite when needed were added and mixed for 2 minutes. The melt mixture was degassed and poured into a mold. After cooling the mold to room temperature, the transparent soap bar is fully solidified and can be cut into the desired final form.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. A transparent soap bar for cleaning the skin comprising:
    about 10 wt. % to about 30 wt. % of a soap surfactant, by weight of the soap bar, wherein the soap surfactant is selected from the group consisting of alkali or alkaline earth metal, and ammonium salts of $C_6$-$C_{18}$ carboxylic acids;
    about 1.5 wt. % to about 30 wt. % of a synthetic surfactant, by weight of the soap bar, wherein the synthetic surfactant is selected from the group consisting of an anionic surfactant, a nonionic surfactant, and mixtures thereof;
    about 0.01 wt. % to about 2 wt. % of a fragrance component, by weight of the soap bar, wherein the fragrance component comprises ketone and/or aldehyde fragrance components;
    about 0.01 wt. % to about 5 wt. % of an amine component, by weight of the soap bar, wherein the amine component is selected from the group consisting of a primary amine, a secondary amine, a tertiary amine, a substituted or unsubstituted 2-pyridinol N-oxide material, an amphoteric surfactant, and mixtures thereof;
    about 0.01 wt. % to about 0.5 wt. % of an antioxidant salt, by weight of the soap bar, wherein the anti-oxidant salt is selected from the group consisting of an alkali metal metabisulfite, an alkali metal sulfite, an alkali metal bisulfite and mixtures thereof; and
    wherein the transparent soap bar has a percent transmittance (% T) value of greater than about 40% as measured according to the Measurement of % Transmittance method.

2. The transparent soap bar of claim 1, wherein the anti-oxidant salt is selected from the group consisting sodium metabisulfite, sodium sulfite, potassium sulfite, sodium bisulfite, potassium bisulfite and mixtures thereof.

3. The transparent soap bar of claim 1, wherein the soap bar comprises about 0.05 wt. % to about 0.4 wt. % of the antioxidant salt by weight of the soap bar.

4. The transparent soap bar of claim 1, wherein the soap surfactant comprises alkali or alkaline earth metal of $C_6$-$C_{18}$ carboxylic acids, wherein the $C_6$-$C_{18}$ carboxylic acid is selected from the group consisting of caproic acid, caprylic acid, capric acid, lauric acid, myristic acid, palmitic acid, margaric acid, stearic acid, myristoleic acid, palmitoleic acid, sapienic acid, oleic acid, elaidic acid, vaccenic acid, linoleic acid, linoelaidic acid, α-linolenic acid, and combinations thereof.

5. The transparent soap bar of claim 4, wherein the soap surfactant comprises a mixture of stearic acid, palmitic acid and lauric acid; and/or sodium salts thereof.

6. The transparent soap bar of claim 1, wherein the soap bar comprises from about 0.2 wt. % to about 5.0 wt. % of the amine component by weight of the soap bar.

7. The transparent soap bar of claim 1, wherein the substituted or unsubstituted 2-pyridinol-N-oxide material is 1-hydroxy-4-methyl-6-(2,4,4-trimethylpentyl)-2-pyridone monoethanolamine salt.

8. The transparent soap bar of claim 1, wherein the amphoteric surfactant is selected from the group consisting of sodium lauroamphoacetate, sodium cocoamphoacetate, disodium lauroamphoacetate, disodium cocoamphodiacetate, cocamidopropyl betaine, lauramidopropyl betaine, and mixtures thereof.

9. The transparent soap bar of claim 8, wherein the amphoteric surfactant is selected from the group consisting of cocamidopropyl betaine, sodium lauroamphoacetate, and mixtures thereof.

10. The transparent soap bar of claim 1, when the amine component is selected from the group consisting of ethanolamine, diethanolamine, triethanolamine, cocamidopropyl betaine, lauramidopropyl betaine, cocamidopropyl hydroxysultaine, lauramidopropyl hydroxysultaine, sodium lauroamphoacetate, piroctone olamine and mixtures thereof.

11. The transparent soap bar of claim 1, wherein the synthetic surfactant comprises an anionic surfactant, wherein the anionic surfactant is selected from the group consisting of: sodium $C_{8-18}$ is alkyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_8$-$C_{18}$ alkyl aminopropionate, sodium laureth-1 sulfate, ammonium laureth-1 sulfate, triethanolamine laureth-1 sulfate, sodium tridecyl benzene sulfonate, sodium dodecyl benzene sulfonate, sodium lauroyl sarcosinate, sodium lauroyl sarcosinate, sodium cocoyl sarcosinate, sodium lauroyl methyl isethionate, sodium lauroyl isethionate, sodium cocoyl isethionate, sodium lauroyl glycinate, sodium cocoyl glycinate, potassium lauroyl glycinate, potassium cocoyl glycinate, sodium lauroyl glutamate, potassium lauroyl glutamate, sodium cocoyl glutamate, potassium cocoyl glutamate, disodium lauroyl glutamate, dipotassium lauroyl glutamate, disodium cocoyl glutamate, dipotassium cocoyl glutamate, sodium lauroyl lactylate and mixtures thereof.

12. The transparent soap bar of claim 1, wherein the synthetic surfactant is a combination of sodium laureth(n) sulfate SLEnS, wherein n is the average moles of ethoxylation, wherein n ranges from 1 to 3 and laureth-6 carboxylic acid.

13. The transparent soap bar o of claim 1, wherein the soap bar comprises from about 0.5 wt. % to about 15 wt. % of an anionic surfactant by weight of the soap bar.

14. The transparent soap bar of claim 1, wherein the soap bar comprises a humectant, wherein the humectant is selected from the group consisting of glycerin, propylene glycol, 1,2-butylene glycol, 1,3-butylene glycol, 1,4-butylene glycol, decylene glycol, polyethylene glycol, sorbitol, sucrose and mixtures thereof.

15. A method of preventing or reducing discoloration of a transparent soap bar, comprising:

adding about 0.01 wt. % to about 0.5 wt. % of an antioxidant salt by weight of the soap bar, wherein the anti-oxidant salt is selected from the group consisting of an alkali metal metabisulfite, an alkali metal sulfite, an alkali metal bisulfite and mixtures thereof; to a premix comprising:

about 10 wt. % to about 30 wt. % of a soap surfactant, by weight of the soap bar, wherein the soap surfactant is selected from the group consisting of alkali or alkaline earth metal, and ammonium salts of $C_6$-$C_{18}$ carboxylic acids;

about 1.5 wt. % to about 30 wt. % of a synthetic surfactant, by weight of the soap bar, wherein the synthetic surfactant is selected from the group consisting of an anionic surfactant, a nonionic surfactant, and mixtures thereof;

about 0.01 wt. % to about 2 wt. % of a fragrance component, by weight of the soap bar, wherein the fragrance component comprises ketone and/or aldehyde fragrance components;

from about 0.01 wt. % to about 5 wt. % of an amine component, by weight of the soap bar, wherein the amine component is selected from the group consisting of a primary amine, a secondary amine, a tertiary amine, a substituted or unsubstituted 2-pyridinol N-oxide material, an amphoteric surfactant, and mixtures thereof;

wherein the resulting transparent soap bar has a percent transmittance (% T) value of greater than about 40% according to the Measurement of % Transmittance method.

* * * * *